US008956341B2

(12) United States Patent
Chen et al.

(10) Patent No.: US 8,956,341 B2
(45) Date of Patent: Feb. 17, 2015

(54) SURGICAL DEVICE WITH REUSABLE HANDLE

(75) Inventors: How-Lun Chen, San Diego, CA (US);
Jesse Crumley, Atlanta, GA (US);
Robert F. Leonard, Furlong, PA (US)

(73) Assignee: CareFusion 2200, Inc., San Diego, CA (US)

( * ) Notice: Subject to any disclaimer, the term of this patent is extended or adjusted under 35 U.S.C. 154(b) by 940 days.

(21) Appl. No.: 12/797,933

(22) Filed: Jun. 10, 2010

(65) Prior Publication Data

US 2011/0306952 A1    Dec. 15, 2011

(51) Int. Cl.
*A61B 17/00* (2006.01)
*A61B 1/32* (2006.01)
*A61B 19/00* (2006.01)
*A61B 17/10* (2006.01)
*A61B 17/29* (2006.01)
*A61B 18/14* (2006.01)

(52) U.S. Cl.
CPC ............ *A61B 17/29* (2013.01); *A61B 18/1445* (2013.01); *A61B 2017/0046* (2013.01); *A61B 2017/292* (2013.01); *A61B 2017/2929* (2013.01); *A61B 2017/293* (2013.01); *A61B 2017/2931* (2013.01); *A61B 2019/4868* (2013.01)
USPC .............. 606/1; 600/204; 606/130; 606/136

(58) Field of Classification Search
CPC ............... A16B 19/22; A61B 19/2203; A61B 2019/2242
USPC ................................ 600/204; 606/130, 1, 136
See application file for complete search history.

(56) References Cited

U.S. PATENT DOCUMENTS

| 4,113,923 | A | | 9/1978 | Cheron |
| 5,312,391 | A | | 5/1994 | Wilk |
| 5,334,198 | A | | 8/1994 | Hart et al. |
| 5,342,359 | A | | 8/1994 | Rydell |
| 5,352,235 | A | | 10/1994 | Koros et al. |
| 5,578,052 | A | | 11/1996 | Koros et al. |
| 5,603,723 | A | | 2/1997 | Aranyi et al. |
| 5,607,449 | A | * | 3/1997 | Tontarra ........................ 606/205 |

(Continued)

FOREIGN PATENT DOCUMENTS

| DE | 297 08 568 U1 | 8/1997 |
| DE | 201 18 882 U1 | 5/2002 |

(Continued)

OTHER PUBLICATIONS

Definition of aperture. Oxiford Dictionaries, retrieved on Jul. 12, 2013; Retrieved from the Internet <http://oxforddictionaries.com/us/definition/american_english/aperture?q=aperture>.*

(Continued)

*Primary Examiner* — William Thomson
*Assistant Examiner* — Sebastian X Lukjan
(74) *Attorney, Agent, or Firm* — Brinks Gilson & Lione

(57) ABSTRACT

A laparoscopic surgical device is provided, including a removable tool-comprising shaft having an outer shaft and an inner actuation rod that may be removably or permanently connected together. A handle of the device includes a two-button mechanism for engaging and releasing the removable tool-comprising shaft. The two-button mechanism is configured to engage overlapping corresponding apertures of the outer shaft and the inner rod that extends through the outer shaft.

19 Claims, 9 Drawing Sheets

(56) References Cited

U.S. PATENT DOCUMENTS

| | | | |
|---|---|---|---|
| 5,611,813 A | 3/1997 | Lichtman | |
| 5,618,304 A | 4/1997 | Hart et al. | |
| 5,669,875 A | 9/1997 | van Eerdenburg | |
| 5,727,428 A | 3/1998 | Lemaire, III et al. | |
| 5,752,972 A | 5/1998 | Hoogeboom | |
| 5,769,841 A | 6/1998 | Odell et al. | |
| 5,827,299 A | 10/1998 | Thomason et al. | |
| 5,951,488 A * | 9/1999 | Slater et al. | 600/564 |
| 5,984,939 A | 11/1999 | Yoon | |
| 6,007,560 A * | 12/1999 | Gottlieb et al. | 606/205 |
| 6,066,146 A | 5/2000 | Carroll et al. | |
| 6,077,290 A | 6/2000 | Marini | |
| 6,086,606 A | 7/2000 | Knodel et al. | |
| 6,340,352 B1 * | 1/2002 | Okada et al. | 601/2 |
| 6,419,640 B1 | 7/2002 | Taylor | |
| 6,595,984 B1 * | 7/2003 | DeGuillebon | 606/1 |
| 6,652,521 B2 | 11/2003 | Schulze | |
| 6,666,854 B1 | 12/2003 | Lange | |
| 6,914,806 B2 | 7/2005 | Kunikiyo | |
| 6,923,783 B2 | 8/2005 | Pasqualucci | |
| 7,341,564 B2 | 3/2008 | Zwiefel et al. | |
| 7,481,824 B2 | 1/2009 | Boudreaux et al. | |
| 2005/0187572 A1 | 8/2005 | Johnston et al. | |
| 2006/0161190 A1 | 7/2006 | Gadberry et al. | |
| 2007/0175953 A1 | 8/2007 | Shelton, IV. et al. | |
| 2007/0244497 A1 | 10/2007 | Ahlberg et al. | |
| 2008/0046001 A1 * | 2/2008 | Renger et al. | 606/205 |

FOREIGN PATENT DOCUMENTS

| | | |
|---|---|---|
| EP | 1 889 578 A2 | 2/2008 |
| JP | 10118090 | 5/1998 |
| JP | 10127652 | 5/1998 |
| JP | 2005034513 A2 | 2/2005 |
| WO | WO 95/07053 | 3/1995 |
| WO | WO 99/03405 A2 | 1/1999 |
| WO | WO 2008/012325 A2 | 1/2008 |

OTHER PUBLICATIONS

Definition of recess. Oxiford Dictionaries, retrieved on Jul. 12, 2013; Retrieved from the the Internet <http://oxforddictionaries.com/us/definition/american_english/recess?q=recess>.*

International Search Report and Written Opinion for PCT/US2011/038506, dated Jul. 19, 2011.

2007 Unpublished description and images of various commercially available laparoscopy instruments.

* cited by examiner

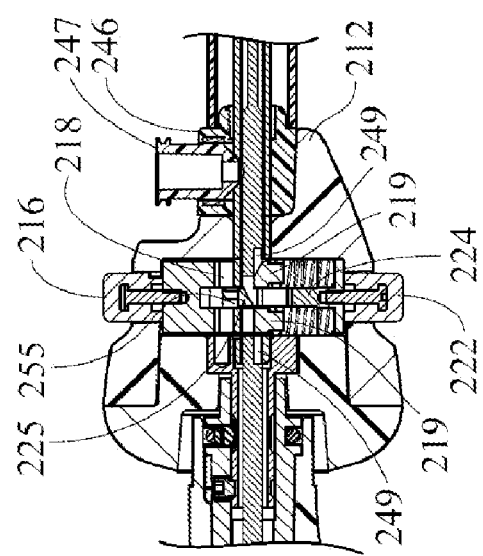
FIG. 3B1

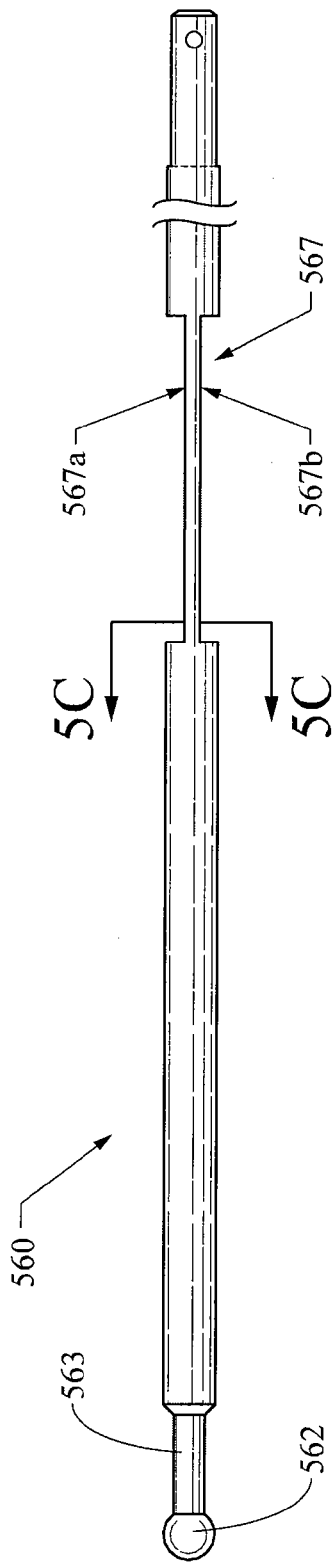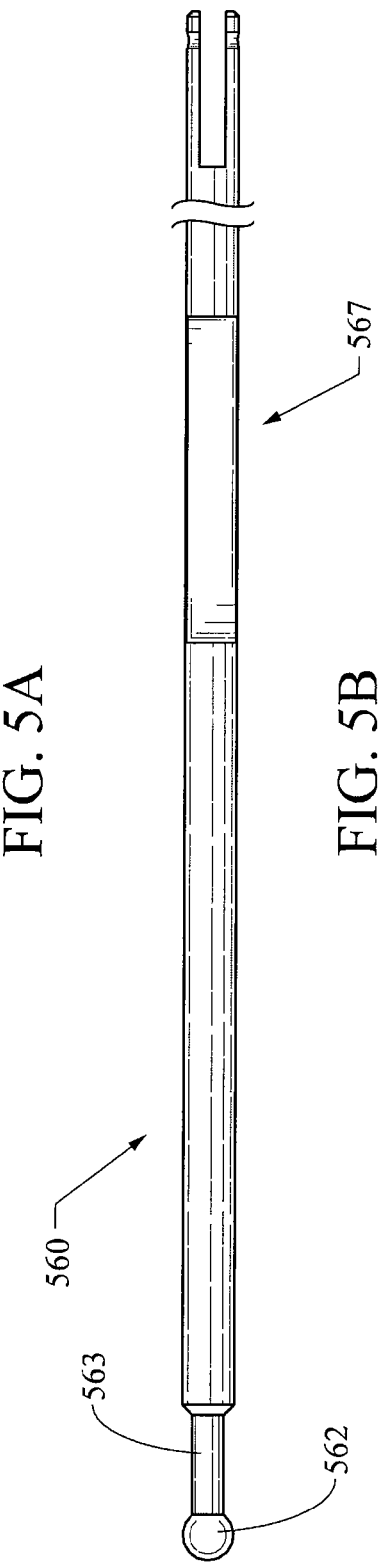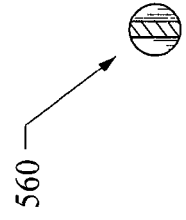

SURGICAL DEVICE WITH REUSABLE HANDLE

FIELD OF THE INVENTION

The present invention relates generally to medical devices, and more particularly to a reusable handle configured to manipulate a removable tool end assembly of a laparoscopic surgical device.

BACKGROUND

As depicted in FIG. 1, a typical monopolar electrosurgical laparoscopic tool device 100 generally has five main components: a handle 102, an outer shaft 104 extending longitudinally from the handle, an actuation rod 106 extending through the outer shaft, an electrode 108 in electroconductive contact with the actuation rod, and an actuatable end effector 110, disposed at the distal end of the device. The handle 102 illustrated is a "ring handle", which has a stationary finger portion 112 attached to the outer shaft 104 and an actuatable thumb portion 114 attached to the actuation rod 106. Actuation of the thumb portion 114 by pivoting relative to the finger portion 112 moves the actuation rod 106 axially within the outer shaft 104 to operate the end effector 110. Although many different variations of each of the above components have been introduced into the art, there exists a need for designs that provide efficiency in manufacturing, and that provide surgeons and other users with ergonomic features to enhance safety and ease of use. In particular, there is a need for a handle design that includes an easy-to-use locking feature that provides for secure attachment and convenient detachment of a tool end assembly.

BRIEF SUMMARY

Embodiments of the present invention are configured to address the needs in the art for ergonomic designs that present advantages in manufacture and use. Preferred embodiments of the present invention may be configured such that they may be cleaned, sterilized, and reused, or they may be disposable. The most preferred embodiments of the present invention include a tool end retention mechanism that is biased so as to engage a one-piece or two-piece tool end assembly, which can be released using a two-button component of the retention mechanism. This retention mechanism provides a secure engagement of an outer shaft and an inner actuation rod of a tool end, as well as a handle that may be reusable. In certain embodiments, reusable tool end assemblies may also be used. While embodiments of the present invention discussed herein are directed to aspects of a handle for a laparoscopic surgical device, those of skill in the art will appreciate that handle embodiments of the present invention may be used with a variety of shaft configurations and end effectors (e.g., needle holders, clamps, scissors, dissectors, graspers), and that such uses may be practiced within the scope of the present invention.

In one aspect, embodiments of a surgical device handle may include a tool end body that includes an inner actuation rod reciprocally disposed through a longitudinal lumen of an outer shaft, where the distal ends of the rod and shaft may be permanently attached or may be removably attached.

BRIEF DESCRIPTION OF THE DRAWINGS

FIG. 5A-5C show, respectively, side, top, and transverse section views of an inner shaft embodiment.

DETAILED DESCRIPTION

Figure 1:
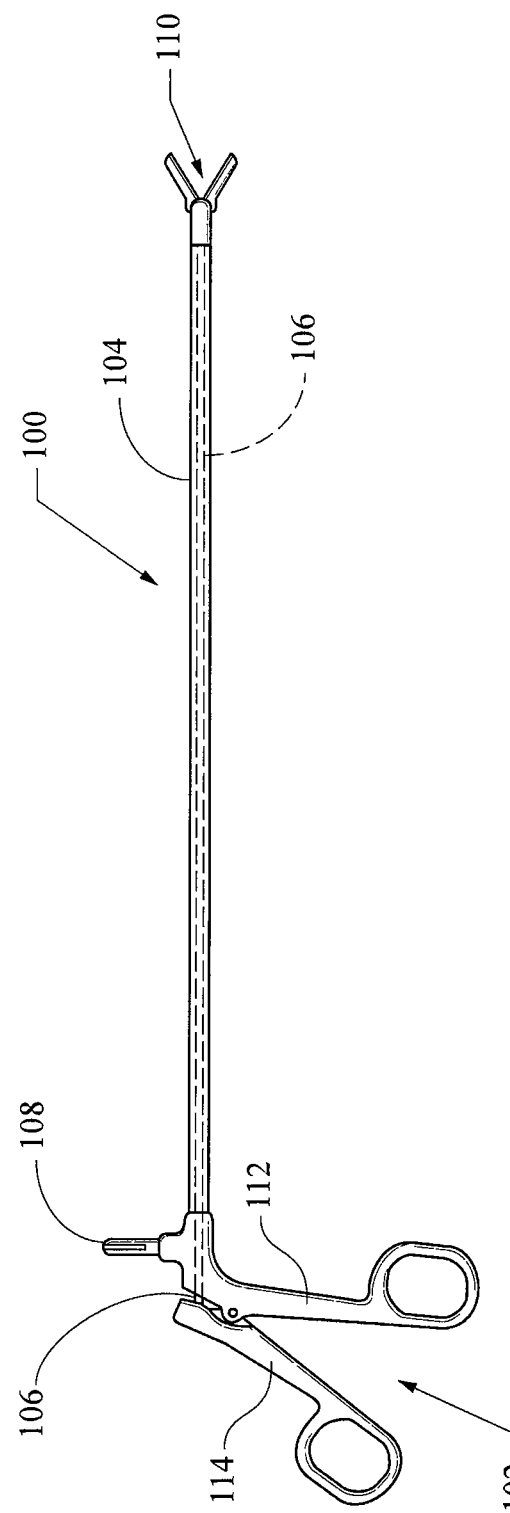
FIG. 1 shows a prior art laparoscopic tool device.
Figure 2:
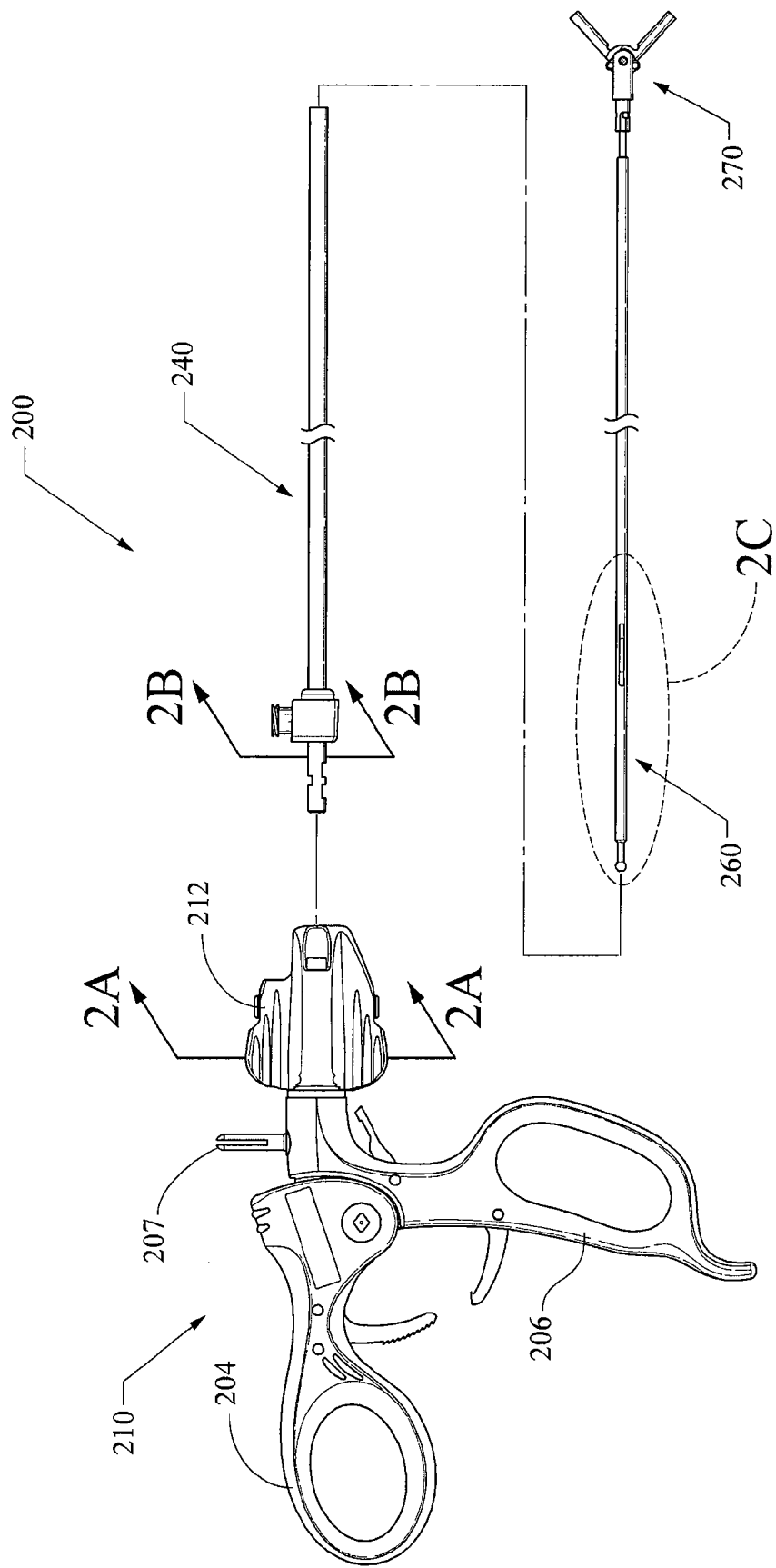
FIG. 2 illustrates a disassembled view of first embodiment of a laparoscopic device.

The exterior of a first embodiment of a laparoscopic surgical device 200 is illustrated with reference to FIGS. 2-2C. As shown in FIG. 2, which is a disassembled view of a "three-piece embodiment," the handle 210 includes a thumb ring member 204 (commonly referred to as a "thumb bow") pivotably attached at a pivot pin 208 to a finger ring member 206 (commonly referred to as a "finger bow"). The handle members 204, 206 preferably are biased away from each other by, for example, a torsion spring or leaf spring. The thumb and finger ring members 204, 206 preferably are constructed of a resin material but may alternatively be constructed of plastic or other materials known in the art to be suitable for multiple sterilizations in an autoclave. A single-use embodiment may be constructed of materials known in the art, but not necessarily configured for multiple sterilizations. The device 200 may be configured as a monopolar or bipolar instrument configured for cutting and coagulation/electrocautery, including a Bovie post 207 or other electrode connection. A knob 212, configured to rotate about its longitudinal axis in an indexed or smooth-rotating manner (various constructions for both of which are well-known in the art), may be included at the distal end of the handle 210.

A tool end body including an elongate tubular outer shaft 240 extends distally from the finger ring member 206. An actuation rod 260 extends distally from the thumb ring member 204 through a longitudinal lumen of the shaft 240 and includes a tool tip 270 at its distal end. At the distal end of the device 200, an end effector 264 is operably connected both to the shaft 240 and the actuation rod 260. The actuation rod connection to the outer shaft 240 may be permanent, or it may be removable (e.g., with a bayonet, threaded, snap-fit, or other connection). The shaft 240 may be constructed of metallic or polymeric materials, and preferably has an electroinsulative coating when the device 200 is configured as an electrosurgical instrument with a length that will most often be rigid, semi-rigid, or have very limited flexibility along its longitudinal axis. The shaft 240 preferably is configured for use with laparoscopy trocars for abdominal or other laparoscopic/minimally invasive surgical techniques (e.g., standard embodiments may have an outer diameter of about 5 mm to about 10 mm). All components of preferred embodiments will be configured to maintain fluid seal conditions desirable for use during a procedure on an insufflated patient. The handle 210 may include one or more ratchet mechanisms configured to assist a user in positioning and operating the device 200. Detailed depictions of handle construction as well as examples of ratchet and other retention/manipulation mechanisms that may be used within the scope of the present invention include those described in U.S. Pat. App. Publ. No. 2007/0299469, to Carpenter et al., which is incorporated herein by reference.

Figure 2A:
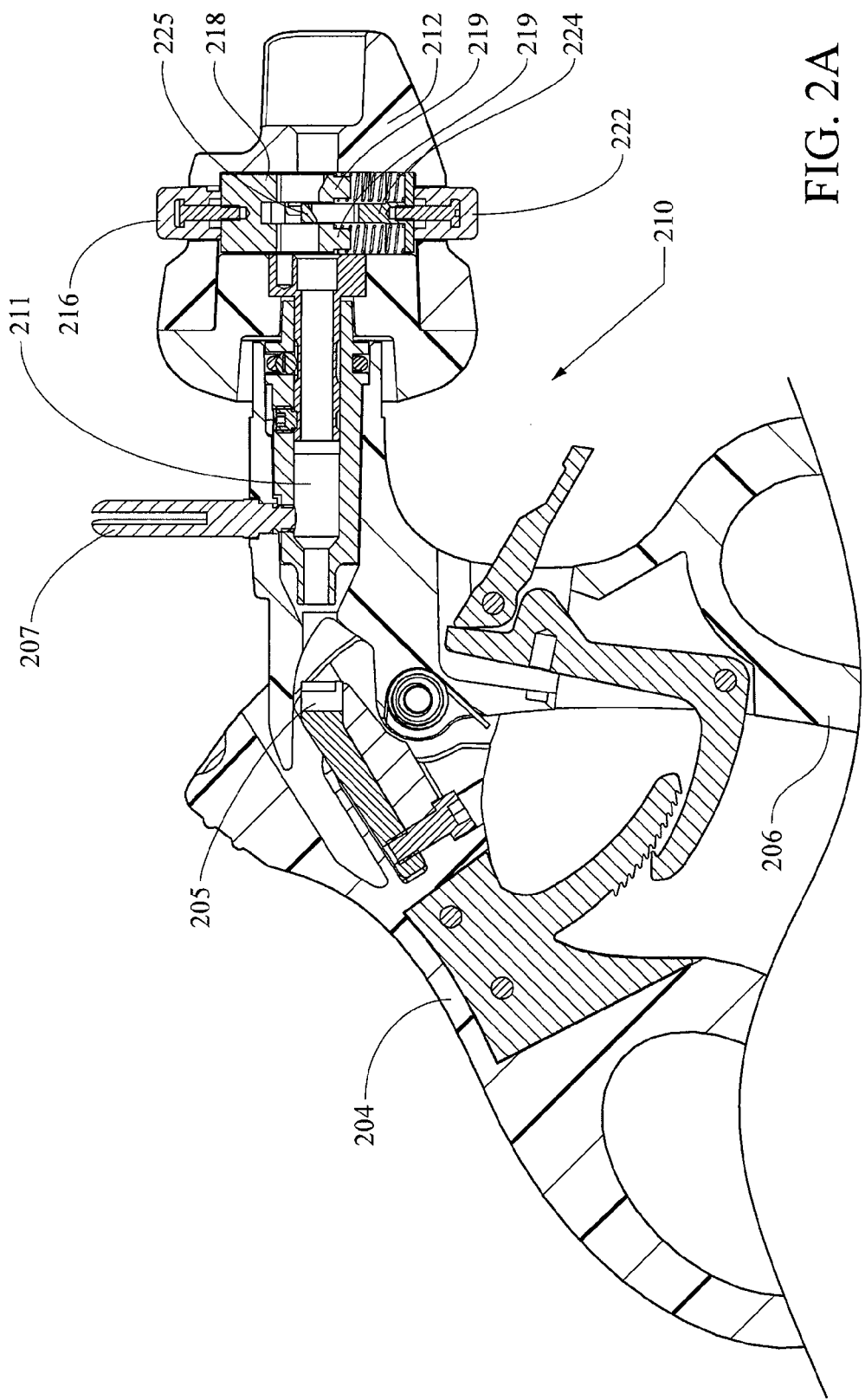
FIG. 2A shows a longitudinal section view, taken along line 2A-2A of FIG. 2, of the tool end retention mechanism of the first handle embodiment.

FIG. 2A is a partial longitudinal section view of the handle 210 along line 2A-2A, showing the handle portion of an engagement mechanism for releasably connecting the tool body shaft 240 to the handle 210. A central channel 211 extends through the knob 212 and the upper portion of the finger bow handle member 206. This channel 211 is configured to receive the proximal ends of the tool body outer shaft 240 and inner actuation rod 260. The thumb ring handle member 204 includes an opening 205 configured as a ball-cage that is configured to capture a proximal-end ball 262 of the actuation rod 260.

The knob 212 substantially houses the shaft-engagement and rod-engagement portions of the engagement mechanism (the ball-cage 205 of the thumb bow 204 not being considered part of the engagement mechanism for purposes of the present description, although it serves an important function in retaining/actuating the inner rod 260). The knob includes two opposing, depressible buttons 216, 222. As shown in FIG. 2A, the first button 216 is attached to and disposed opposite a two-toothed retaining member 218, which includes teeth 219 that are biased up toward the first button 216 into the channel 211. The second button 222 is attached to and disposed opposite a one-toothed retaining member 224, which includes a tooth 225 that is biased down toward the second button 222 into the channel 211. As shown, the retaining members and their teeth (which collectively may be referred to as "shutters") are permanently attached to the handle 210 and in direct mechanical communication with their respective/corresponding buttons. Actuation of the retaining members is described below with reference to FIGS. 3A-3B. The bias for each of the retaining members is shown as being provided by coil springs, but other biasing means may be used, as known in the art.

Figure 2B:
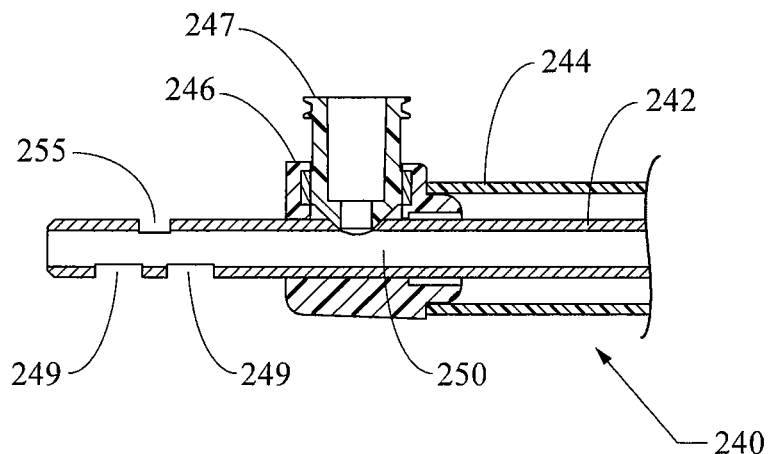
FIG. 2B is a longitudinal sectional view of a proximal portion of the tool end body shaft assembly taken along line 2B-2B of FIG. 2.

FIG. 2B shows a longitudinal section view (taken along line 2B-2B of FIG. 2) of the proximal portion of the tool end body shaft assembly 240. In this embodiment, an inner portion 242 of the shaft 240 is metal, and an outer covering portion 244 includes an electroinsulative polymer. In the embodiment shown, which is a "larger outer diameter" embodiment, the outer covering 244 is separated from the inner portion 242 of the shaft 240, but—in certain "smaller outer diameter" embodiments, the outer covering 244 may be directly in contact with and/or be constructed as an overlay of the inner shaft portion 242. A nose portion 246, configured to be received in a complementarily shaped cavity of the knob 212 is mounted near the proximal shaft end. The nose portion 246 includes a flush port 247 that provides fluid communication with a longitudinal lumen 250 extending through the length of the shaft 240. A proximal endmost portion of the shaft 240, which is configured to be received into the handle channel 211, includes at least first and second apertures that are at least partially opposed to each other. In the embodiment shown in FIGS. 2-3C, the first aperture is embodied as a pair of apertures 249 configured to align with and receive the first retaining member teeth 219. The second aperture is embodied as an aperture 255 that is disposed opposite the first aperture and is configured to align with and receive the second retaining member tooth 225.

Figure 2C:
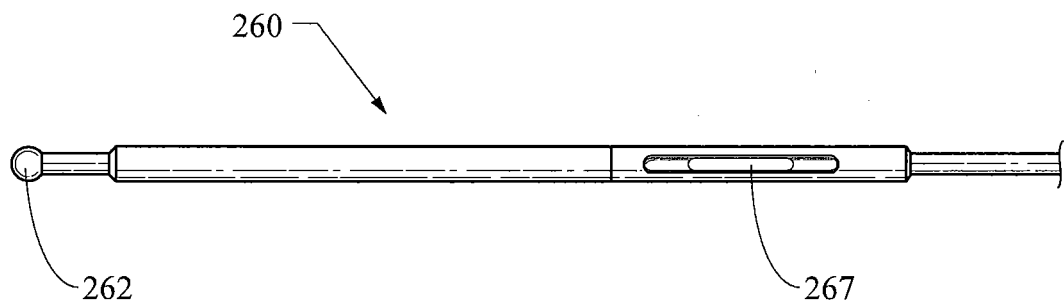
FIG. 2C shows a detail view of a proximal end portion of the actuation rod of the device of FIG. 2.

FIG. 2C shows an external top-down view of the proximal portion of the actuation rod 260. A ball 262 or other flared structure is disposed at its proximal end, configured for capture by the upper end of the thumb-ring handle member 204. The ball 262 may include a larger outer diameter than a majority length of the rod 260 and most preferably includes a larger outer diameter than a rod portion immediately distally adjacent the ball. The inner rod 260 is configured to be slidably disposed through the shaft lumen 250. As shown, a proximal rod length may include a larger outer diameter than a majority length of the rod 260 that will facilitate flushing of the shaft lumen 250 with the rod not being removed therefrom while providing a desirable proximal seal therebetween. Pivoting actuation of the thumb bow 204 relative to the finger bow 206 will longitudinally reciprocate the inner rod 260 relative to the shaft 240. At its distal end the rod 260 includes a tool assembly 270 that is configured to be attached to the outer shaft 240. This attachment may be removable, as is described below with reference to FIG. 3C, or it may be permanent such that the shaft 240 and rod 260 may be attached/removed from the handle 210 as a single unit. Embodiments where the rod and shaft are permanently connected may be configured to have the distal rod/shaft/tool assembly disposable after a single use or configured to be cleaned and/or sterilized. Many different tool tip assemblies 270 are known in the prior art for use/actuation with a reciprocating inner rod and an outer shaft that is relatively fixed. Tool tips may include clamps, graspers, cutting scissors, or other actuatable tool tips currently known or later-developed, while being practiced within the scope of the present invention. The inner rod 260 may be constructed as a single piece, or in multiple pieces, including that one or more portions (in addition to the proximal ball 262 may have a larger outer diameter than a majority length of the rod).

A proximal region of the rod 260 includes an elongate inner rod groove or aperture 267. The inner rod aperture 267 is shown as generally obround, but may have varied internal geometry including that it may be embodied as a pair of opposing grooves that do not go all the way through the rod (not shown, but easily able to be understood by those of skill in the art as including a longitudinal wall between the opposed faces of the aperture 267). It is configured to receive the ends of the first and/or second retaining member teeth 219, 225. When the teeth 219, 225 are engaged with the inner rod aperture 267, they will allow it to reciprocate longitudinally, but will generally prevent the rod 260 from rotating about its longitudinal axis. As such, when the teeth 219, 225 are engaged through the outer shaft apertures 249, 255 into the inner rod aperture 267, they (the teeth) will: (i) generally maintain the outer shaft 240 in a fixed longitudinal and rotational position relative to the handle 210; and (ii) generally maintain the inner rod 260 in a fixed rotational position relative to the outer shaft 240 and handle 210 while permitting it to reciprocate longitudinally relative to the handle 210 and outer shaft 240 upon pivoting actuation of the thumb bow 204 relative to the finger bow 206. This structure and its related functionality are described below with reference to a method of assembling the device 200.

Figure 3A:
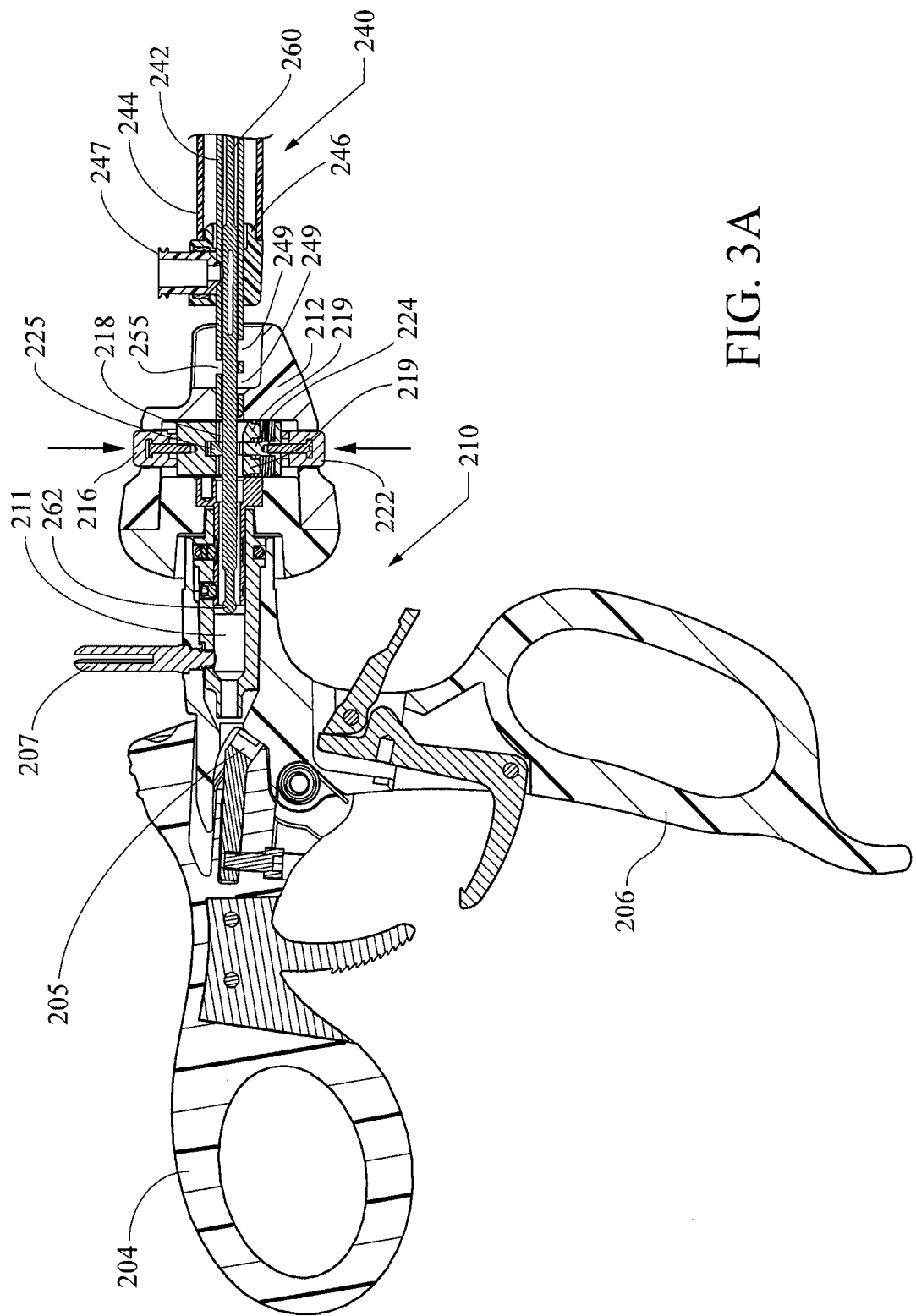
FIGS. 3A-3B show a section view as in FIG. 2A, illustrating a method of assembly, with FIG. 3B1 providing a detailed call-out view of the mechanism that is substantially within the index knob of FIG. 3B.
Figure 3B:
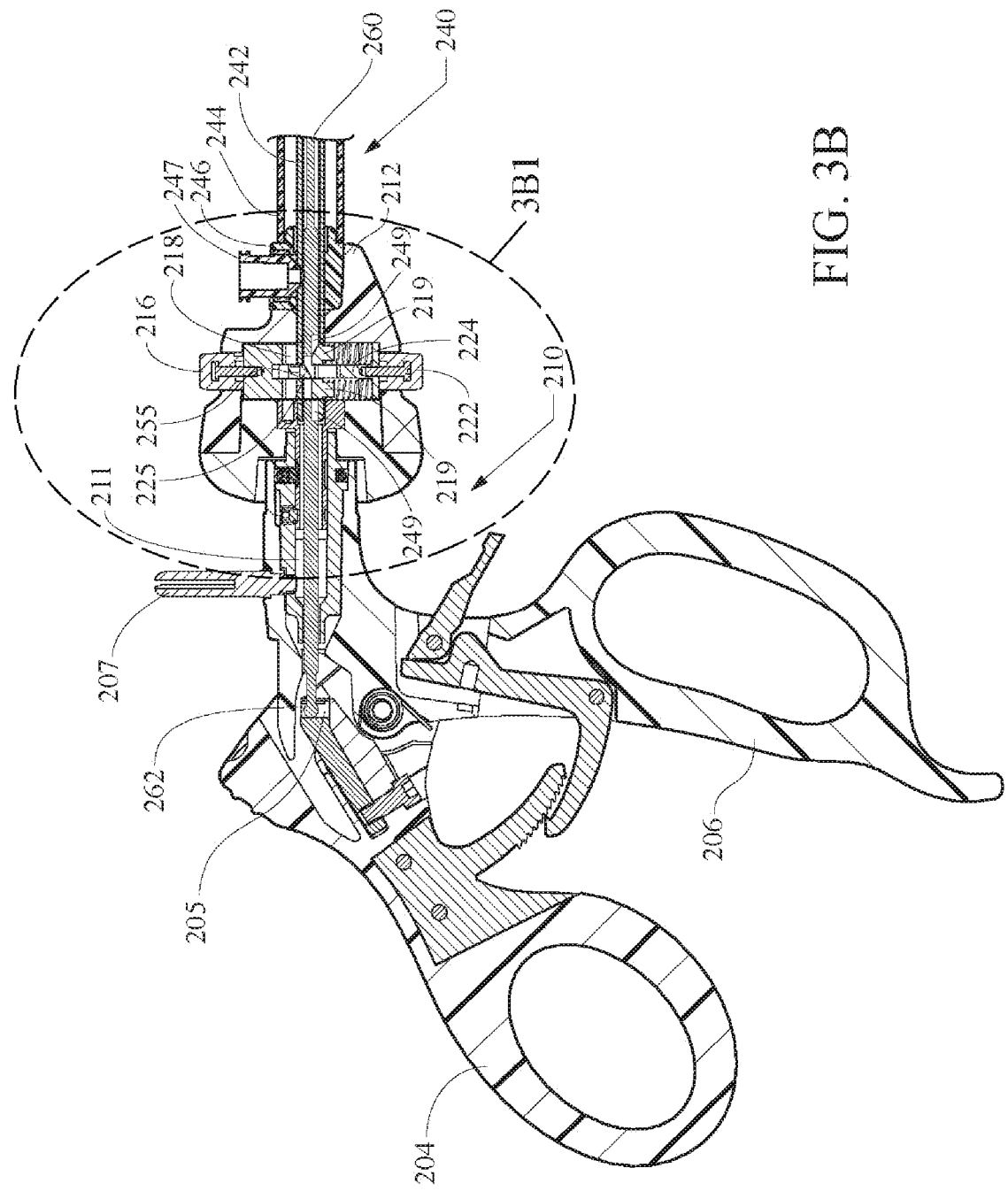

In most embodiments, the thumb bow 204 will be rotatable relative to the finger bow 206 in only a single plane. However, handle constructions are known in the art, where out-of-plane rotation maybe used. Preferred embodiments of the device 200 will include insulative material over all handle and other proximal-region surfaces that are likely to conduct current when the device is configured as an electrosurgical device and attached to an electrosurgical power supply. As shown in FIG. 3B, discussed below, in embodiments where a nose portion is used, it is permanently fixed to the outer shaft and will prevent the outer shaft from rotating relative to the engagement mechanism (whether that engagement mechanism is disposed in an indexing knob, as shown, or disposed in a fixed portion of the handle assembly 210).

A method of assembling the device 200 of FIGS. 2-2C is described with reference to FIGS. 3A-3C. In FIG. 3A, the thumb bow 204 is over-rotated up and away from the finger bow 206. This orientation exposes a top end opening of the ball-cage 205 in line with the proximal end of the longitudinal handle channel 211. The inner rod 260 is disposed through the shaft lumen 250 and longitudinally directed into the handle channel 211. The first and second buttons 216, 222 are depressed in toward the central longitudinal axis of the engagement mechanism in the indexing knob 212. This actuation of the first button 216 pushes the teeth 219 of the two-toothed retaining member 218 down and out of the handle channel 211. Likewise, this actuation of the second button 222 pushes the tooth 225 of the second retaining member 224 up and out of the handle channel 211.

With the retaining teeth 219, 225 held out of the way, the handle channel 211 allows the inner rod 260 and outer shaft 240 to be advanced proximally thereinto until the proximal ball 262 of the rod enters and is captured by the ball-cage 205. As shown in FIG. 3A, one or more of the teeth 219, 225 may have an angled, cambered, or rounded distal surface such that the rod 260 and/or shaft 240 can more readily approach, dislodge, and pass the teeth, even if the buttons 216, 222 are not initially fully depressed. The thumb bow 204 can be released and directed/pivoted down toward the finger bow 206, fully capturing the ball 262 in the ball-cage 205, which has a key-hole cross section such that a broader proximal portion engages the ball 262 while a narrower distal portion prevents the ball from being released distally when the thumb bow 204 is rotated down as shown in FIG. 3B. The ball-cage 205 preferably will not interfere with actuation of the handle members nor of rotation of the inner rod 260 about its longitudinal axis. The elongate inner rod aperture 267 is visible in FIG. 3A, with the rod 260 and outer shaft 240 being shown about 90 degrees out of the rotational position that will allow the retaining teeth 219, 225 to engage that inner rod aperture 267 through the outer shaft apertures 249, 255.

FIG. 3B shows the tool body assembly including the outer shaft 240 and inner rod 260 as being fully advanced proximally. The shaft 240 and rod 260 have been rotated and the buttons 216, 222 have been released so that: (i) the shaft apertures 249, 255 are aligned with the inner rod aperture 267; (ii) the retaining teeth 219, 225 are extended into their respective biased positions to engage the inner rod aperture 267 through the outer shaft apertures 249, 255; and (iii) the nose portion 246 is aligned and engaged with the indexing knob 212. As shown in this engaged configuration/position, the inner rod 260 will reciprocate longitudinally relative to the outer shaft 240 and finger bow 206, which are longitudinally fixed relative to each other. In embodiments where the indexing knob 212 is rotatable, the knob 212, outer shaft 240, and inner rod 260 can rotate relative to the handle 210 about their mutual longitudinal axis.

Figure 4:
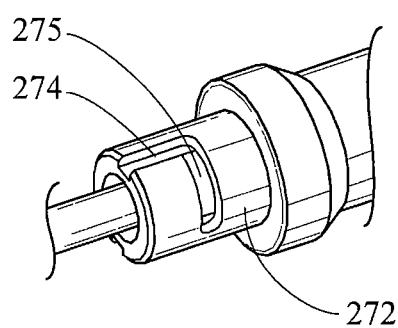
FIG. 4 shows a detail perspective view from FIG. 3C.
Figure 3C:
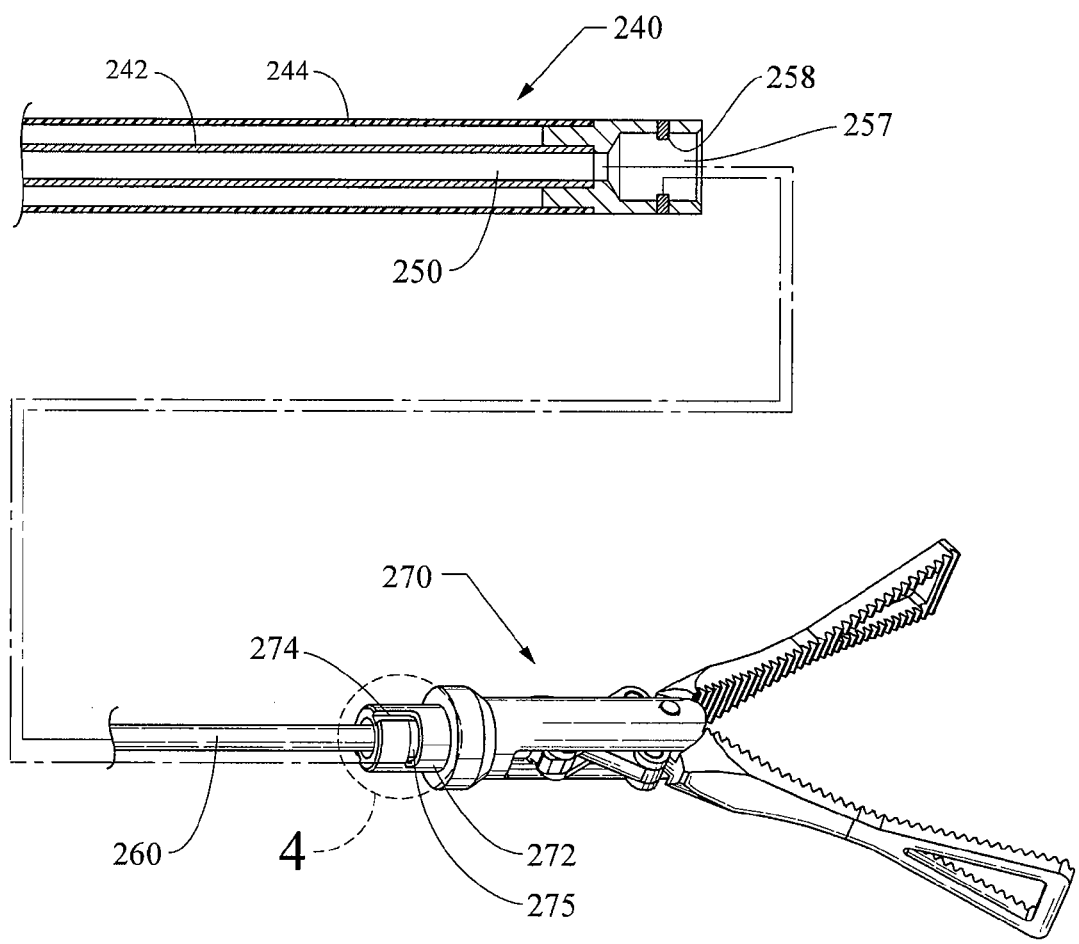
FIG. 3C shows a distal end connection embodiment between the actuation rod and tool end shaft body.

FIG. 3C shows one connection construction for embodiments of the device 200 wherein the inner rod 260 is removable from the outer shaft 240 rather than being permanently distally attached thereto. The tool tip 270 is shown as a grasper assembly, but may be constructed as cutting scissors, biopsy forceps, or any number of other laparoscopy-type tool tips. The proximal base 272 of the tool tip body is generally cylindrical and includes a bayonet groove having a longitudinal groove portion 274 and a radial groove portion 275. The inner rod 260 is axially movable relative to the base 272. FIG. 3C also shows the distal end of the outer shaft 240, which includes a distal opening 257 configured to snugly receive the tip base 272. A groove-engaging pin 258 extends radially into the opening 257. FIG. 4 shows a perspective detail view of FIG. 3C.

When the actuation rod 260 is directed into the shaft lumen 250, the groove engaging pin 258 can be guided to the distal end of the longitudinal bayonet groove portion 274, then the tool tip can be rotated to engage the pin 258 to the end of the radial groove portion 275. The bayonet mechanism including the pin and groove preferably is constructed such that when the pin 258 is fully engaged at the end of the groove 275, the rotational position of the inner rod 260 aligns its proximal aperture 267 with the outer shaft apertures 249, 255. It should be appreciated that one, two or more bayonet pins and grooves may be used in various embodiments. In other embodiments, a threaded connection including a Luer-like connection requiring only a fractional turn for engagement (e.g., quarter-turn) or traditional multi-twist threading, snap-fit, reverse-bayonet, and/or other connection structures may be used to effect a connection between the distal ends of the shaft 240 and rod 260, without departing from the scope of the present invention. Whether or not the rod and shaft are engaged with a handle, it is preferable that a distal connection of the outer shaft is configured to engage the distal regions of the inner rod and the outer shaft when the inner shaft aperture is rotationally aligned with at least one of the outer rod apertures.

FIGS. 5A-5C show another embodiment of an inner actuation rod 560. It includes a proximal-end ball 562 with a region 563 immediately distally adjacent the ball 562 that has a smaller outer diameter than the next adjacent portion of the rod 560, and that transitions thereto with a circumferential face oriented at about a 45-degree angle relative to a longitudinal central axis of the rod 560. Rather than the aperture 267 discussed above with reference to an inner rod embodiment 260, this embodiment includes a narrowed rod portion 567 having a generally transverse rectangular cross-sectional geometry as shown in FIG. 5C (which is a section view of FIG. 5A taken along line 5C-5C).

It will be appreciated that this rod embodiment may be used in conjunction with a handle such as the handle 210 described above. In such an application, the teeth 219, 225 may engage the faces 567a, 567b of the narrowed portion 567 (when oriented relatively horizontal as shown in FIG. 5A), or they may modified to include generally vertical longitudinal grooves (not shown) configured to be engaged with/about the narrowed rod portion 567 (in an embodiment where the flat portion is oriented relatively vertical as shown in FIG. 5B; of course, the distal end in each of FIGS. 5A-5B may be configured differently to appropriately engage a tool tip/end effector as is well-known in the art).

Those of skill in the art will appreciate that there are known means for controlling the relative position/bias of the ratchet members disclosed above that are appropriate for use within the scope of the present invention, and that different materials may be useful in embodiments of the present invention. Those of skill in the art will also appreciate that, for handle embodiments of the present invention, the thumb ring member and/or the finger ring member may not actually require a closed ring structure, but may include an open ring or other-shaped support structure for a user's thumb and fingers, respectively. It is intended that the foregoing detailed description be regarded as illustrative rather than limiting.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. A surgical instrument, comprising:
   a handle comprising:
      a first handle member;
      a second handle member pivotably attached to the first handle member, configured to pivot relative thereto;
   a body comprising:
      a tubular outer shaft removably attached to the first handle member;
      an inner rod extending through a longitudinal lumen of the outer shaft and removably attached to the second handle member in a manner permitting reciprocal longitudinal movement relative to the outer shaft; and
   an engagement mechanism configured to provide a releasable connection between the handle and the body, comprising:
      at least a first outer shaft aperture and a second outer shaft aperture, which are at least partially opposed to each other and are disposed through a proximal region of the outer shaft;
      a first shutter permanently actuatably attached to the first handle member and biased into a releasable engagement with the at least a first outer shaft aperture;
      a second shutter permanently actuatably attached to the first handle member, at least partially opposed to the first shutter, and biased into a releasable engagement with the at least a second outer shaft aperture;
   wherein the instrument is configured such that pivoting one of the first and second handle members relative to the other longitudinally moves the inner rod relative to the outer shaft; and
   wherein the inner rod further comprises a proximal inner rod aperture that is configured to align with the at least one of the outer shaft apertures and to receive at least one of the first and second shutters while allowing the inner rod to move longitudinally relative to the outer shaft when the handle is actuated by pivoting one of the handle members relative to the other.

2. The surgical instrument of claim 1, wherein the handle further comprises an indexing knob configured to rotate the body about its longitudinal axis, and wherein—when the instrument is assembled—the indexing knob substantially houses the engagement mechanism.

3. The surgical instrument of claim 1, wherein the first and second shutters are operatively associated with first and second buttons, respectively, wherein actuation of each of said buttons is configured to oppose the bias of its corresponding shutter and move it out of an engagement with a corresponding outer shaft aperture.

4. The surgical instrument of claim 1, further comprising a tool tip attached to a distal portion of the outer shaft and the inner rod.

5. The surgical instrument of claim 4, wherein the attachment to the outer shaft is removable.

6. The surgical instrument of claim 1, further comprising a first button in direct mechanical communication with the first shutter and configured so that actuation of the first button opposes the bias of the first shutter and moves it out of an engagement with the first outer shaft aperture.

7. The surgical instrument of claim 6, further comprising a second button in direct mechanical communication with the second shutter and configured so that actuation of the second button opposes the bias of the second shutter and moves it out of an engagement with the second outer shaft aperture.

8. The surgical instrument of claim 1, wherein a proximal end of the inner rod includes a greater outer diameter than a majority length of the inner rod.

9. The surgical instrument of claim 8, wherein the second handle member comprises an opening configured to capture and retain the proximal end of the inner rod.

10. The surgical instrument of claim 1, wherein the inner rod further comprises a distal connection with the outer shaft configured to engage the inner rod to the outer shaft when the inner rod aperture is rotationally aligned with at least one of the outer shaft apertures.

11. A handle for a laparoscopic surgical instrument, the handle comprising:
   a first handle member;
   a second handle member pivotably attached to the first handle member, configured to pivot relative thereto along a single plane; and
   an engagement mechanism configured to provide a releasable connection between the first handle member and a shaft body, the engagement mechanism comprising:
      a body-receiving channel configured to longitudinally receive a proximal end of a shaft body;
      a first shutter permanently actuatably attached to the first handle member and biased to extend at least partially into the body-receiving channel, where the first shutter is attached to and disposed opposite a first reciprocating button configured to actuate the first shutter opposite its bias;
      a second shutter permanently actuatably attached to the first handle member, at least partially opposed to the first shutter, and biased to extend at least partially into the body-receiving channel;
   wherein the second handle member includes an opening configured to capture and retain a proximal end of an actuation rod.

12. The handle of claim 11, wherein the first handle member comprises an indexing knob configured to rotate relative thereto about a longitudinal axis of the body-receiving channel.

13. The surgical instrument of claim 12, wherein the engagement mechanism is comprised by the indexing knob, and the first reciprocating button extends reciprocally depressibly therefrom.

14. The surgical instrument of claim 11, further comprising an inner actuation rod removably attached at a proximal rod end to the second handle member.

15. The surgical instrument of claim 14, wherein a distal end of the actuation rod comprises a surgical tool tip.

16. The surgical instrument of claim 15, further comprising an outer shaft removably attached at a proximal shaft end to the first handle member.

17. The surgical instrument of claim 16, wherein a distal end of the outer shaft is removably attached to the tool tip.

18. The surgical instrument of claim 16, wherein a distal end of the outer shaft is permanently attached to the tool tip.

19. A surgical instrument, comprising:
a handle;
a body extending distally from the handle and comprising:
- a tubular outer shaft removably attached to the handle;
- an inner rod extending through a longitudinal lumen of the outer shaft and removably attached to the handle in a manner permitting reciprocal longitudinal movement relative to the outer shaft; and an engagement mechanism configured to provide a releasable connection between the handle and the body, comprising:
- at least a first outer shaft aperture and a second outer shaft aperture, which are at least partially opposed to each other and are disposed through a proximal region of the outer shaft;
- a first shutter permanently actuatably attached to the handle and biased into a releasable engagement with the at least a first outer shaft aperture and with a longitudinal inner rod aperture that permits longitudinal reciprocation of the inner rod relative to the first shutter without movement of the tubular outer shaft; and
- a second shutter permanently actuatably attached to the handle, at least partially opposed to the first shutter and biased into a releasable engagement with the at least a second outer shaft aperture.

* * * * *